(12) United States Patent
Okada et al.

(10) Patent No.: US 8,043,220 B2
(45) Date of Patent: Oct. 25, 2011

(54) ULTRASONOGRAPH

(75) Inventors: Kazutaka Okada, Chiba (JP); Hiroshi Kanda, Saitama (JP); Tsuyoshi Otake, Kashiwa (JP); Tsuyoshi Kimura, Chiba (JP); Tatsuya Hayashi, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1309 days.

(21) Appl. No.: 10/512,472

(22) PCT Filed: Apr. 3, 2003

(86) PCT No.: PCT/JP03/04285
§ 371 (c)(1),
(2), (4) Date: Oct. 26, 2004

(87) PCT Pub. No.: WO03/090625
PCT Pub. Date: Nov. 6, 2003

(65) Prior Publication Data
US 2006/0058677 A1    Mar. 16, 2006

(30) Foreign Application Priority Data
Apr. 26, 2002    (JP) .................................. 2002-126075

(51) Int. Cl.
*A61B 8/14*    (2006.01)
(52) U.S. Cl. ...................................................... 600/459
(58) Field of Classification Search .................... 600/443
See application file for complete search history.

(56) References Cited

U.S. PATENT DOCUMENTS

| | | | | |
|---|---|---|---|---|
| 4,534,221 A | * | 8/1985 | Fife et al. .................. | 73/626 |
| 5,243,993 A | * | 9/1993 | Alexander et al. ......... | 600/520 |
| 5,517,996 A | * | 5/1996 | Okada et al. ............... | 600/447 |
| 5,582,173 A | * | 12/1996 | Li ............................... | 600/443 |
| 5,724,976 A | * | 3/1998 | Mine et al. .................. | 600/459 |
| 5,891,040 A | * | 4/1999 | Grenon et al. .............. | 600/455 |

(Continued)

FOREIGN PATENT DOCUMENTS

EP    1 231 481 A2    8/2002

(Continued)

OTHER PUBLICATIONS

Japanese Office Action, dated Nov. 30, 2010, issued in corresponding Japanese Patent Application No. 2008-098933.

*Primary Examiner* — Tse Chen
*Assistant Examiner* — Hien Nguyen
(74) *Attorney, Agent, or Firm* — Antonelli, Terry, Stout & Kraus, LLP.

(57) ABSTRACT

An ultrasound diagnostic apparatus includes an ultrasound probe, a transmission unit for transmitting an ultrasound signal to an object to be examined via the ultrasound probe, a reception unit for processing a signal received by the ultrasound probe, and an image generating unit for generating an image on the basis of the received signal processed by the reception unit, wherein the transmission unit has a function of transmitting the ultrasound signals with varying frequency plural times in an identical direction at predetermined time intervals. The ultrasound signal transmitted plural times includes a first waveform in which the frequency increases and a second waveform in which the frequency decreases, and the reception unit has a function of phasing and adding received signals respectively corresponding to the first waveform and the second waveform, whereby, in tissue harmonic imaging, the penetration is improved, while the resolution is maintained.

12 Claims, 8 Drawing Sheets

U.S. PATENT DOCUMENTS

| | | | |
|---|---|---|---|
| 5,913,823 A * | 6/1999 | Hedberg et al. | 600/443 |
| 5,933,389 A | 8/1999 | Hossack et al. | |
| 6,038,925 A * | 3/2000 | Ohtani et al. | 73/598 |
| 6,110,119 A * | 8/2000 | Hall | 600/455 |

FOREIGN PATENT DOCUMENTS

| | | |
|---|---|---|
| EP | 1 358 849 A1 | 11/2003 |
| JP | 05-043257 | 2/1993 |
| JP | 05146444 A * | 6/1993 |
| JP | 405146444 A * | 6/1993 |
| JP | 10-179589 | 7/1998 |
| JP | 2000-300554 | 10/2000 |
| JP | 2001-008933 | 1/2001 |
| WO | WO 01/21074 A1 | 3/2001 |

* cited by examiner

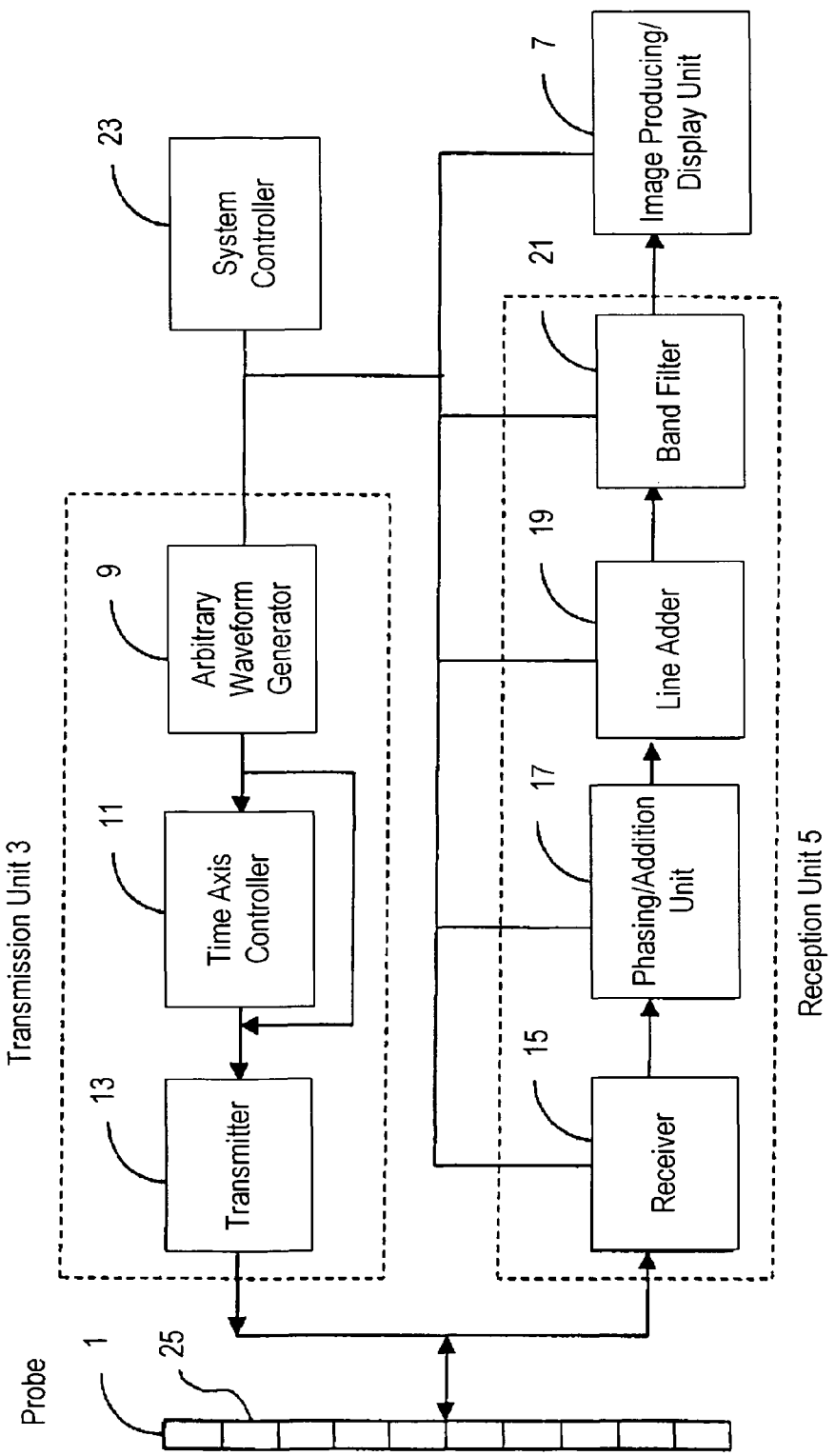

Reception from Shallow Portion

Reception from Deep Portion

ULTRASONOGRAPH

TECHNICAL FIELD

The present invention relates to an ultrasound diagnostic apparatus, and, more particularly, to an ultrasound diagnostic apparatus for imaging a harmonic component that is generated when ultrasound is propagated inside a body of an object to be examined.

BACKGROUND OF THE INVENTION

An ultrasound diagnostic apparatus is designed to transmit an ultrasound signal inside an object to be examined and to obtain information available in diagnosis, e.g. a tomographic image, on the basis of a received signal, including an echo signal of the transmitted signal. It has been reported that, in the technique of displaying a tomographic image, a high-contrast image can be obtained by imaging a harmonic component (e.g. frequency $2f_0$ or $3f_0$) as opposed to a fundamental component (frequency $f_0$) of the transmitted signal. An imaging method of this type is referred to as "Tissue Harmonic Imaging."

The above-described harmonic component is generated due to nonlinear distortion occurring mainly when the ultrasound is propagated inside the object. That is, a signal of the ultrasound irradiated to the inside of living body is distorted during propagation in tissue due to a nonlinear response of the tissue, and the harmonic component is increased. As a result, the echo signal includes, e.g. a double frequency $2f_0$ and a triple frequency $3f_0$ of a fundamental component $f_0$.

In tissue harmonic imaging, it is important how to extract an echo of a strong harmonic component. The conventionally reported methods of tissue harmonic imaging include one referred to as a "filtering technique", for example.

This technique is designed to extract the harmonic component of e.g. $2f_0$ from a received signal using a band pass filter with a central frequency of e.g. $2f_0$. Another example is a method referred to as a "pulse inversion technique," which is designed to emphasize the second harmonic component by transmitting first and second waveforms having a mutually alternated polarity at predetermined time intervals, and phasing and adding the echo signals thereof to cancel the fundamental component. Further, for example, Japanese Unexamined Patent Publication No. 2002-34976 discloses a technique of extracting a harmonic component through a filter from received signals obtained from transmitted signals having two different center frequencies, and widening the band of the harmonic component by combining those extracted signals, thus improving the resolution and enhancing the signal strength in a beam depth direction, as well as suppressing generation of motion artifacts. However, because the frequency of the harmonic component in an ultrasound signal is higher than that of the fundamental component, the harmonic component is sensitive to attenuation of the signal during propagation. Accordingly, the degree of an echo signal received from a deep portion, i.e. the penetration, is undesirable. Meanwhile, when the center frequency $f_0$ of the fundamental component is lowered, the echo signal is scarcely affected by the attenuation, whereby the penetration can be improved. However, the resolution is deteriorated, as is generally known.

SUMMARY OF THE INVENTION

The present invention has been devised in consideration of the above-described factors, and an object thereof is to improve the penetration, while maintaining the resolution.

To achieve the above-stated object, an ultrasound diagnostic apparatus according to the present invention includes an ultrasound probe, a transmission unit for transmitting an ultrasound signal to an object to be examined via the ultrasound probe, a reception unit for processing a signal received by the ultrasound probe, and an image generating unit for generating an image on the basis of the received signal processed by the reception unit, wherein the transmission unit has a function of transmitting the ultrasound signal having a varying frequency plural times in one direction at predetermined time intervals. This ultrasound signal transmitted plural times includes a first waveform in which the frequency increases and a second waveform in which the frequency decreases, and the reception unit has a function of phasing and adding received signals corresponding to the first waveform and the second waveform.

Accordingly, in comparison with a conventional case where a waveform having a frequency $f_0$ is transmitted while its polarity is alternated, a frequency spectrum of the received signal after phasing and addition changes, whereby a component in a frequency band between $f_0$ and $2f_0$ can be emphasized. Because the component in this frequency band has a frequency lower than $2f_0$, it is scarcely affected by attenuation, and so the penetration is desirable. Accordingly, by extracting this frequency component to generate an image based thereon, the penetration in the tissue harmonic imaging can be improved without lowering $f_0$, i.e., without lowering the resolution.

Here, the waveform having a varying frequency may be formed by, e.g., joining each one cycle or a plurality of cycles of waveforms having different frequencies. Alternatively, it may be formed by joining parts of ½, ¼, or ⅛ cycle of the waveforms having different frequencies, or a chirp waveform in which the frequency sequentially changes may be used.

In this case, the above-described frequency spectrum is varied by variably setting a change rate of frequency variation of the first waveform and the second waveform. Here, particularly when diagnostic information is acquired from a deep portion inside the object (portion distant from the probe), the frequency spectrum of a received signal is desirably shifted so as to be low in consideration of the penetration. Then, it is desirable that the transmission unit has a function of variably setting a transmission focus depth, and the change rate of frequency variation of the first waveform and the second waveform is variably set depending on the transmission focus depth.

Further, in this case, when the first waveform and the second waveform respectively shift so that their signal strengths decrease, the above-described spectrum variation can be emphasized. At this time, it is also desirable that the change rate of the signal strengths of the first waveform and the second waveform is variably set depending on the transmission focus depth.

Further, it is also desirable that the polarities of the first waveform and the second waveform are mutually alternated, and the reception unit has a function of phasing and adding the reception signals corresponding to the first waveform and the second waveform after amplifying or attenuating them with a gain difference.

Even when the above-described technique is utilized, the frequency spectrum of the received signal, after phasing and addition, changes, and the component in the frequency band between $f_0$ and $2f_0$ can be emphasized, whereby the penetration can be improved without lowering $f_0$, i.e., without lowering the resolution. In this case, the gain difference may be variably set depending on the reception timing, i.e., the a reception focus depth. For instance, it is desirable that the reception signals corresponding to the first waveform and the second waveform are subjected to a time gain control with different correlation curves between reception timing and gain.

Further, the reception unit may have a function of performing a reception focus processing on the received signal and include a filter for extracting a predetermined frequency band of the received signal, in which the frequency band is variably set depending on the predetermined reception focus depth. According thereto, it is possible to adapt to the spectrum variation of the received signal occurring due to the difference in the reception focus depth, i.e. the difference in depth of the portion examined inside the object, and to extract a component in a preferable frequency band.

Further, in the case where the change rate of the varying frequency or signal intensity of the first waveform and the second waveform according to the predetermined transmission focus depth is variably set, a frequency band of the filter may be variably set in accordance with the transmission focus depth in order to adapt to the spectrum variation of a received signal caused by varying the frequencies or the signal intensities, as mentioned above.

BRIEF DESCRIPTION OF THE DRAWINGS

FIG. 1 is a block diagram showing the structure of an ultrasound diagnostic apparatus according to a first embodiment of the present invention.

BEST MODE FOR CARRYING OUT THE EMBODIMENT

Embodiment 1

Figures 2A, 2B:
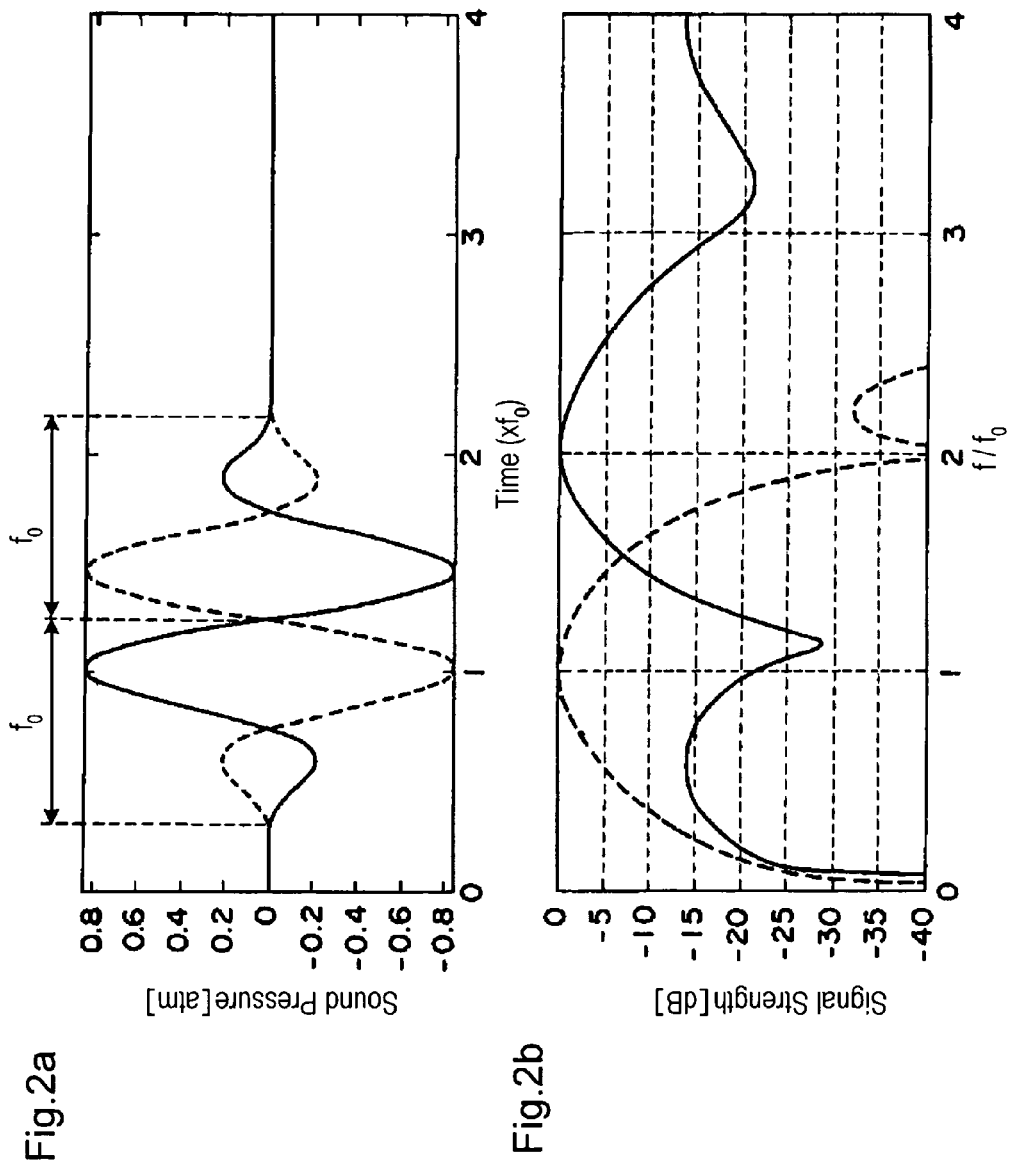
FIGS. 2a and 2b are graphs presenting the simulation results of waveforms of a transmitted signal and spectrums of the transmitted signal and a received signal based on a conventional pulse inversion method.

Hereinafter, an ultrasound diagnostic apparatus according to a first embodiment of the present invention will be described. FIG. 1 is a block diagram showing the structure of the ultrasound diagnostic apparatus according to this embodiment. As shown in FIG. 1, the ultrasound diagnostic apparatus includes an ultrasound probe 1, a transmission unit 3 for transmitting an ultrasound signal to an object to be examined (not shown in the figure) via the ultrasound probe 1, a reception unit 5 for receiving a received signal including an echo signal from the object via the ultrasound probe 1 and for processing the received signal, and an image producing/display unit 7 for generating and displaying a diagnostic image on the basis of the received signal processed by the reception unit 5. The image producing/display unit 7 includes a video processing unit for performing detection, compression, and the like, a Doppler processing unit, and a scan converter, which are not shown in the figure.

The transmission unit 3 includes an arbitrary waveform generator 9 having a function of generating a transmitted signal combining a plurality of waveforms respectively having a predetermined amplitude, frequency, and starting phase, a time axis controller 11 having a function of time-inverting the waveform output by the arbitrary waveform generator 9, and a transmitter 13 having a power amplifier, for supplying a driving signal to the ultrasound probe 1 in response to an output signal of the time axis controller 11. Meanwhile, time axis controller 11 has a so-called first-in/first-out function and a first-in/last-out function using the output of the arbitrary waveform generator 9 as an input signal, and it has a shift register for these functions.

Reception unit 5 receives a signal output from ultrasound probe 1, and it includes a receiver 15 having a pre-amplifier, a time gain control (TGC) amplifier, and an A/D converter, which are not shown in the figure. The reception unit 5 further includes a phasing/addition unit 17 for phasing and adding received signals of channels output by receiver 15 corresponding to the respective transducers of the ultrasound probe 1 and for outputting the added signals as an RF line signal; a line adder 19 for keeping the received signal previously output from phasing/addition unit 17, RF-adding it and a time-delayed received signal output afterward from phasing/adding unit 17, in consideration of their phase, and outputting the resultant signal; and a band pass filter 21 having a function of performing a band pass digital filter calculation for extracting a particular frequency band signal from among the output signals of the line adder 19. A so-called digital beam former is used as the phasing/addition unit 17 to minimize distortion occurring in the addition processing. Further, the system controller 23 is provided for totalizing and controlling operations of each component in the transmission unit 3, the reception unit 5, and the image producing/display unit 7 described above. Further, ultrasound probe 1 includes a plurality of transducers 25 arranged to face the object (not shown) in a line or in a plane.

Next, the operation of the above-described ultrasound diagnostic apparatus will be described. First, arbitrary waveform generator 9 generates and outputs a waveform of a transmitted signal on the basis of a command received from the system controller 23. The waveform of the signal output by the arbitrary waveform generator 9 is formed by combining waveforms in which the frequency is time-sequentially varied. This point will be described later in more detail. A signal output by the arbitrary generator 9 is input to the time axis controller 11. And, the first waveform is output without being time-inverted by the first-in/first-out function. After that, the time axis controller 11 outputs a second waveform formed by inverting the first waveform symmetrically about a line perpendicular to a time axis by the first-in/last-out function with a time delay relative to the first waveform. Transmitter 13 performs a known transmission focus processing on the basis of the first waveform and the second waveform, and it generates and outputs a driving signal to each transducer 25 of the ultrasound probe 1. A transducer 25 that is supplied with the driving signal from transmitter 13 via a transmission/reception separating circuit (not shown) is respectively oscillated to generate an ultrasound wave, and ultrasound beams proceeding in a direction in which the wave surfaces of the respective ultrasound waves transmitted by transducers 25 coincide with each other are formed inside the object (not shown).

On the other hand, the ultrasound signal propagating inside the object as an ultrasound beam is reflected at a portion having a different acoustic impedance inside the object. The reflected signals return to the ultrasound probe 1 and are received as a received signal. The received signals are converted from sound waves into electric signals by the transducer 25 and are input to receiver 15 via the transmission/reception separating circuit (not shown). In receiver 15, the received signal of a channel corresponding to each transducer 25 is amplified by the pre-amplifier and the TGC amplifier, is A/D converted, and then output. A signal output from receiver 15 is input to phasing/addition unit 17, subjected to a known dynamic focus processing for sequentially correcting any variation in reception timing of the received signal between the respective channels occurring due to a difference in the distance from a generating portion of the received signal to each transducer 25, and the processed signals are added and output. Those processings concerning the ultrasound reception are performed on each of the received signals corresponding to the first waveform and the second waveform. The received signals corresponding to the first waveform and the second waveform are combined by line adder 19, temporarily keeping and time-delaying the received signal corresponding to the first waveform and adding it and the received signal corresponding to the second waveform, and are output as a combined received signal. In band pass filter 21, a component of the predetermined frequency band of the combined received signal is extracted. Then, the image producing/display unit 7 generates and displays an ultrasound diagnostic image on the basis of a signal of the extracted frequency band component. That is, the ultrasound diagnostic apparatus carries out the above-described operations while performing scans in the beam direction, and the image producing/display unit 7 performs video processings, including detection and compression, Doppler signal processing, scan conversion and the like, to produce a known B-mode or Doppler-mode image. Meanwhile, the system controller 23 not only controls the above-described series of operations, but also generates data for arbitrary waveform generator 9.

Next, the first waveform, the second waveform, and the frequency spectrums of a transmitted signal and received signal according to this embodiment will be described. First, for easy understanding of the characteristics of this embodiment, the simulation results of the first waveform, the second waveform, and the frequency spectrums of a transmitted signal and the received signal in the conventional pulse inversion method, which are shown in FIGS. 2a and 2b, will be described. FIG. 2a is a graph presenting the first waveform and the second waveform, in which the horizontal axis indicates time and the vertical axis indicates sound pressure of the transmitted wave. Here, the first waveform is presented by a full line and the second waveform is presented by a broken line. As shown in FIG. 2a, both the first waveform and the second waveform are sequences of sine waves for two cycles having the same frequency $f_0$ (2 MHz), to both of which a Hanning weight is applied to simulate a waveform in a living body. The polarity of the first waveform is opposite to that of the second waveform. That is, the sound pressure decreases at the start of a signal with the polarity of the first waveform, and with the polarity of the second waveform, the sound pressure increases.

FIG. 2b is a graph presenting the frequency spectrum of the transmitted signal and the received signal obtained by phasing and adding the received signals corresponding to the first waveform and the second waveform. In the graph, the horizontal axis indicates a frequency ratio ($f/f_0$) in relation to $f_0$=2.0 MHz and the vertical axis indicates signal strength (dB). In FIG. 2b, the spectrum of the transmitted signal is presented by a broken line and that of a combined reception signal is presented by a full line.

As shown in FIG. 2b, in the spectrum of the transmitted signal, the signal strength increases when the frequency increases from 0, and it has its first peak at frequency $f_0$, where it becomes maximal. And, when the frequency further increases, the signal strength then decreases and becomes −40 dB of the first peak at frequency $2f_0$. When the frequency further increases from frequency $2f_0$, the signal strength again increases and has its second peak in the vicinity of frequency $2.3f_0$, and again decreases after that. The signal strength of the second peak is approximately −32 dB of the first peak.

Meanwhile, the spectrum of the combined reception signal has its peaks where the signal strength becomes maximal in the vicinity of $0.6f_0$, $2f_0$, and $4f_0$, and has its nadirs where the signal strength becomes minimal in the vicinity of $1.2f_0$ and $3.3f_0$. Among the peaks, the signal strength is maximized at the peak in the vicinity of $2f_0$, and both signal strengths at the peaks in the vicinity of $0.6f_0$ and $4f_0$ are −14 dB of the signal strength at the peak in the vicinity of $2f_0$. On the other hand, the signal strengths at the nadirs in the vicinity of $1.2f_0$ and $3.3f_0$, where the signal strength becomes minimal, are respectively about −28 dB and −21 dB of that at the peak at $2f_0$.

Figures 3A, 3B:
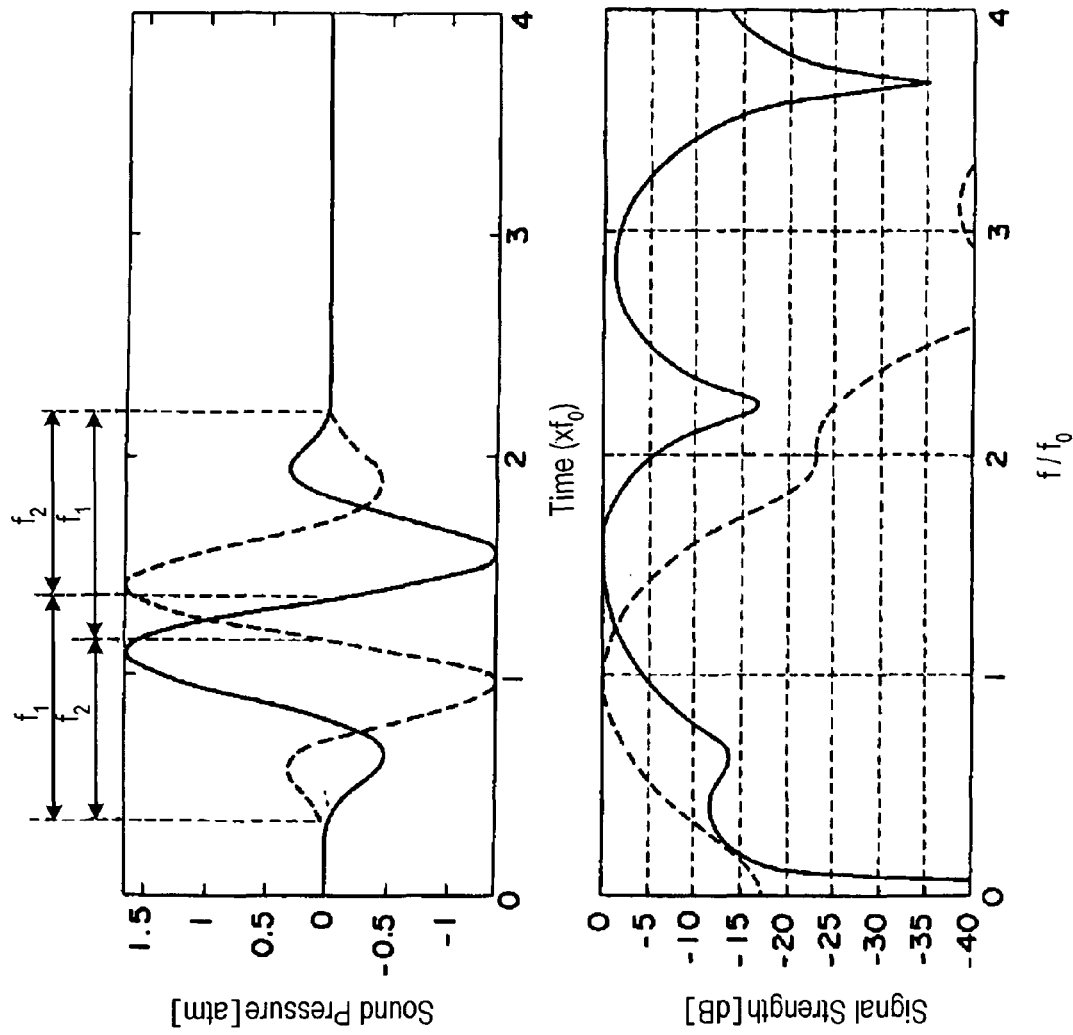
FIGS. 3a and 3b are presenting the simulation results of waveforms of a transmitted signal and spectrums of the transmitted signal and a received signal in the ultrasound diagnostic apparatus of FIG. 1.

Next, one example of the first waveform and the second waveform having varying frequencies and the frequency spectrums of a transmitted signal and a received signal in the ultrasound diagnostic apparatus according to this embodiment of the present invention will be described with reference to the simulation results shown in FIGS. 3a and 3b. FIG. 3a is a graph showing the first waveform and the second waveform, where the horizontal axis indicates time and the vertical axis indicates sound pressure. Here, the first waveform is presented by a solid line and the second waveform is presented by a broken line. As shown in FIG. 3a, the first waveform is formed by joining a first cycle of frequency $f_1$(=1.8 MHz) and a second cycle of frequency $f_2$(=2.2 MHz) with a polarity in which the sound pressure increases at the start of the signal. On the other hand, the second waveform is formed by joining a first cycle of frequency $f_2$ and a second cycle of frequency $f_1$, in which the waveform shifts at a certain change rate between those cycles, and with a polarity in which the sound pressure decreases at the start of signal. Furthermore, a Hanning weight similar to the waveform shown in FIG. 2a is applied to both those first and second waveforms. In other words, the second waveform is formed by time-inverting the first waveform.

FIG. 3b is a graph showing the frequency spectrums of the transmitted signal and a received signal obtained by phasing and adding received signals corresponding to the first waveform and the second waveform, wherein the horizontal axis indicates the frequency ratio ($f/f_0$) in relation to $f_0$=2.0 MHz and the vertical axis indicates signal strength (dB), as in FIG. 2b. In the graph of FIG. 3b, the spectrum of the transmitted signal is presented by a broken line and that of the received signal obtained by phasing and addition is presented by a solid line.

As shown in FIG. 3b, in the spectrum of the transmitted signal, the signal strength increases when the frequency increases from 0 and has its peak where it becomes maximal at frequency $f_0$. When the frequency further increases, the signal strength decreases. After the decreasing rate of signal strength becomes small in the vicinity of frequency $2f_0$ and then becomes 0, the signal strength again decreases, while the decreasing rate increases. Meanwhile, the signal strength in the vicinity of the frequency $2f_0$ is approximately −23 dB relative to the peak at frequency $f_0$.

On the other hand, in the spectrum of the phased and added received signal, the signal strength has its peaks where it becomes maximal in the vicinity of $0.4f$, $1.6f_0$, and $2.8f_0$, and has its nadirs where it becomes minimal in the vicinity of $0.7f_0$, $2.2f_0$, and $3.7f_0$. Among the peaks where the signal strength becomes maximal, the signal strength is maximized at the peak in the vicinity of $1.6f_0$. The signal strengths at the peaks in the vicinity of $0.4f_0$ and $2.8f_0$ are respectively about −12 dB and −2 dB of the signal strength at the peak at $1.6f_0$. Meanwhile, among the nadirs where the signal strength becomes minimal, the signal strength is approximately −14 dB in the vicinity of $0.7f_0$, −17 dB in the vicinity of $2.2f_0$, and −35 dB in the vicinity of $3.7f_0$.

As is clear from a comparison of FIG. 3b with FIG. 2b, in the conventional pulse inversion method, a frequency component in the vicinity of $2f_0$ is most emphasized when the received signals corresponding to the first waveform and the second waveform are combined. Meanwhile, the peak of signal strength comes into the vicinity of $1.6f_0$ by differently determining $f_1$ and $f_2$, and the frequency spectrum thus shifts so as to be low.

On the other hand, in the ultrasound diagnostic apparatus according to this embodiment, the difference $\Delta f(=|f_1-f_2|)$ between frequencies $f_1$ and $f_2$ is variably set depending on the predetermined transmission focus depth. Specifically, $\Delta f$ is variably set so that the frequency spectrum of the signal combining the received signals corresponding to the first waveform and the second waveform shifts so as to be low as the transmission focus depth becomes deep. Meanwhile, the average frequency of the frequencies $f_1$ and $f_2$ is fixed to be $f_0$. When the transmission focus depth is shallow, the transmission and reception are performed while $\Delta f$ is set to be 0, as in the conventional pulse inversion method. $\Delta f$ is varied as the transmission focus depth becomes deep and a transmitted wave is generated so that the above-mentioned peak of the frequency spectrum shifts from $2f_0$ to e.g. $f_0$, desirably from $2f_0$ to, e.g. $1.5f_0$. For example, in the case of performing a multiple transmission focus to complete a received signal for one beam line by combining a plurality of ultrasound beams having different transmission focus depths, $\Delta f$ is variably set depending on the focus depth of each beam. For example, when the focusing is performed on three points, $\Delta f$ on each point is set so that the peaks of its frequency spectrum are at e.g. $2f_0$, $1.8f_0$, and $1.6f_0$ in the ascending order of focus depth. This setting of $\Delta f$, depending on the transmission focus depth, can be carried out by simulation or experiment using an ultrasonic phantom.

Further, in the ultrasound diagnostic apparatus according to this embodiment, a frequency pass band of band pass filter 21 is variably set depending on the variation of the above-described frequency spectrum. Specifically, in order to adapt to the spectrum shift of a received signal after phasing and addition, the frequency pass band is shifted so as to be low as the transmission focus depth becomes deep.

Figure 4A:
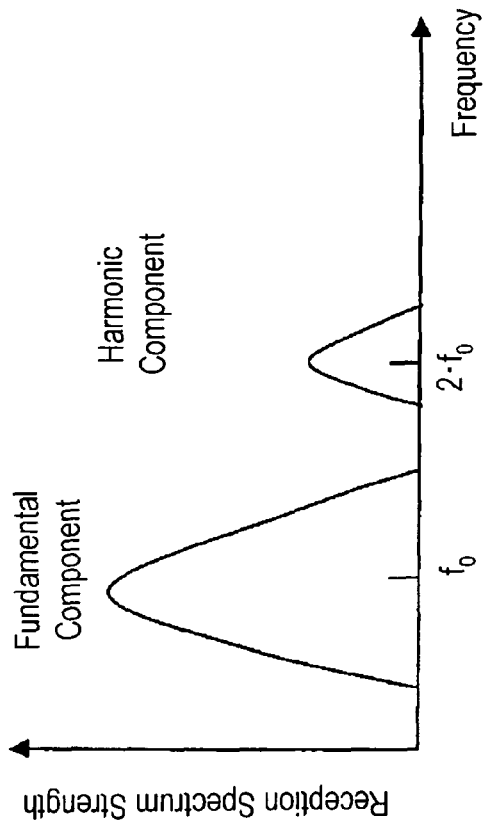
FIGS. 4a and 4b are graphs showing variation of a reception spectrum occurring due to a depth of received signal generation.
Figure 4B:
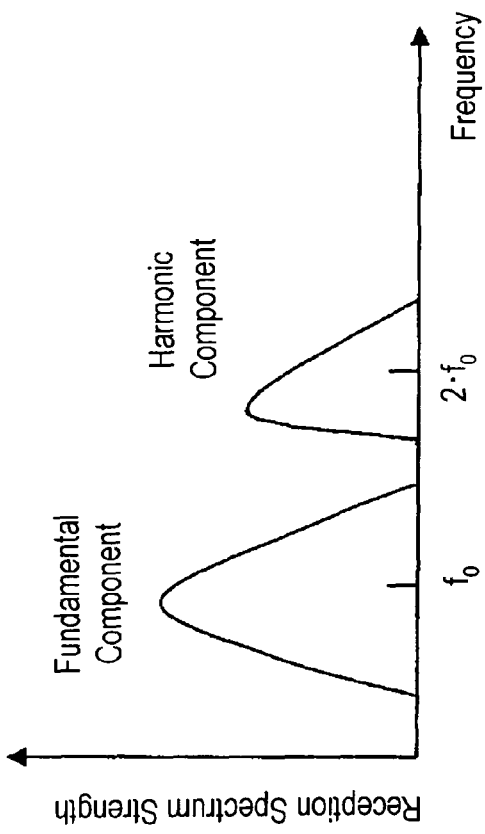

Further, the frequency pass band of the band pass filter 21 is variably set depending on the reception focus depth, even when the transmitted signal is not changed. FIGS. 4a and 4b are graphs showing a reception spectrum of a signal received from a shallow portion of the object, i.e. a portion close to the ultrasound probe, and a reception spectrum of a signal received from a deep portion of the object, i.e. a portion distant from the ultrasound probe. In FIGS. 4a and 4b, only $2f_0$ is presented as a harmonic component for easy understanding. Since the transmitted signal is a pulse wave having usually a few cycles, the spectrum has a certain degree of band around $f_0$ and $2f_0$, as seen in FIGS. 4a and 4b. As shown in FIG. 4b, in the spectrum of a received signal from a deep portion, the harmonic component is increased by a nonlinear distortion occurring when the ultrasound propagates in the living body. However, in the spectrum distribution of the harmonic component, the frequency spectrum shifts so as to be low and the center frequency lowers because a higher frequency component is more sensitive to the attenuation in propagation. Therefore, to deal with this, the frequency pass band of the band pass filter 21 is set to shift to be low as the reception focus depth becomes deeper in conjunction with the dynamic focusing in reception. Specifically, in the case of using a digital FIR filter as the band pass filter 21, its coefficient is desirably set variably in conjunction with the reception focus depth.

As described above, according to this embodiment, by phasing and adding the received signals respectively corresponding to the first waveform in which the frequency shifts so as to increase and the second waveform in which the frequency shifts so as to decrease, the frequency component in the band between $f_0$ and $2f_0$ is emphasized. Accordingly, the waveform is less affected by the attenuation than in the conventional pulse inversion method of emphasizing $2f_0$, whereby the penetration can be improved in a deep portion of focus. Besides, since the $2f_0$ component is imaged, the resolution can be maintained in a shallow portion.

Further, since the change rate of frequency variation of the first waveform and the second waveform is variably set depending on the transmission focus depth, it is possible to emphasize a relatively high-frequency component at a shallow focus depth in consideration of contrast and to emphasize a relatively low frequency component at a deep focus depth in consideration of penetration, whereby a desirable image can be produced depending on the predetermined transmission focus depth.

Further, a frequency band pass filter calculation is performed on the received signal after phasing and addition to variably set the frequency pass band depending on the transmission focus depth, whereby the frequency band to be emphasized can be extracted in response to the change rate of frequency variation of the transmitted wave.

Further, since the frequency pass band is variably set also depending on the reception focus depth, a frequency band can be extracted in response to the spectrum variation of a received signal occurring due to a difference in attenuation of the signal caused by a difference in the propagation distance.

Further, for example, when a relatively shallow portion where the penetration is not a critical problem is examined, an image may be produced by extracting a component of frequency higher than $2f_0$. For example, although in FIG. 3b there is a peak also in the vicinity of $2.8f_0$, the signal strength at the peak where the frequency is larger than $2f_0$ may be extracted using a band pass filter and used in image generation. According thereto, a desirable image contrast can be obtained when a shallow portion is examined.

Further, when a shallow portion is examined, the center frequency of the transmitted signal may be set to be high. In the example of FIGS. 3a and 3b, the center frequency is set as $f_0=2.0$ MHz and the first waveform and the second waveform are $f_1=1.8$ MHz and $f_2=2.2$ MHz, respectively. However, they may be set such that the center frequency $f_0=2.1$ MHz, $f_1=2.0$ MHz, and $f_2=2.2$ MHz. According thereto, a high-contrast image can be obtained at a relatively shallow depth where the penetration is not a problem.

Meanwhile, according to the above-described embodiment, the second waveform is obtained by time-inverting the first waveform using the time axis controller. However, when the arbitrary waveform generator can directly generate the second waveform, the time axis controller is unnecessary.

Further, according to the above-described embodiment, the first waveform and the second waveform are respectively formed by joining waveforms for two cycles. However, they may be formed by joining waveforms for three or more cycles. For example, the first waveform may be formed by joining each one cycle of the waveforms of $f_1=1.8$ MHz, $f_2=2.0$ MHz, and $f_3=2.2$ MHz, and the second waveform may be obtained by time-inverting the first waveform. In this manner, when the first waveform is a combination of each one cycle of the center frequency $f_1, f_2 \ldots f_n, \ldots f_N$ ($N \geq 2$), where $f_1 < f_2 < \ldots < f_n < \ldots < f_N$, and the second waveform is an inversion of the first waveform relative to the time axis, the effect of the invention is not lost even if N=4. However, because the difference between those two transmission waves becomes relatively small when the wave number increases, it can be that the invention is especially effective when N<6.

Further, according to the above-described embodiment, the first waveform and the second waveform are formed by combining sine waves in which the frequency is varied at every one cycle. However, the frequency may be varied at every two or more cycles. Alternatively, it may be frequently changed, such as at every ½ cycle or ¼ cycle, or it may be a so-called chirp waveform in which the frequency sequentially changes.

Embodiment 2

Next, a second embodiment of the ultrasound diagnostic apparatus according to the present invention will be described. The same points as those, enumerated in the description of the first embodiment will not be mentioned, again, and only the differences will be described. The ultrasound diagnostic apparatus according to this embodiment is characterized in that the amplitude of both the first waveform and the second waveform is changed. That is, this embodiment is characterized in that the amplitude of waveform in the first cycle of the first waveform and the second waveform is respectively preset to be larger than that of the subsequent waveform.

Figure 5A:
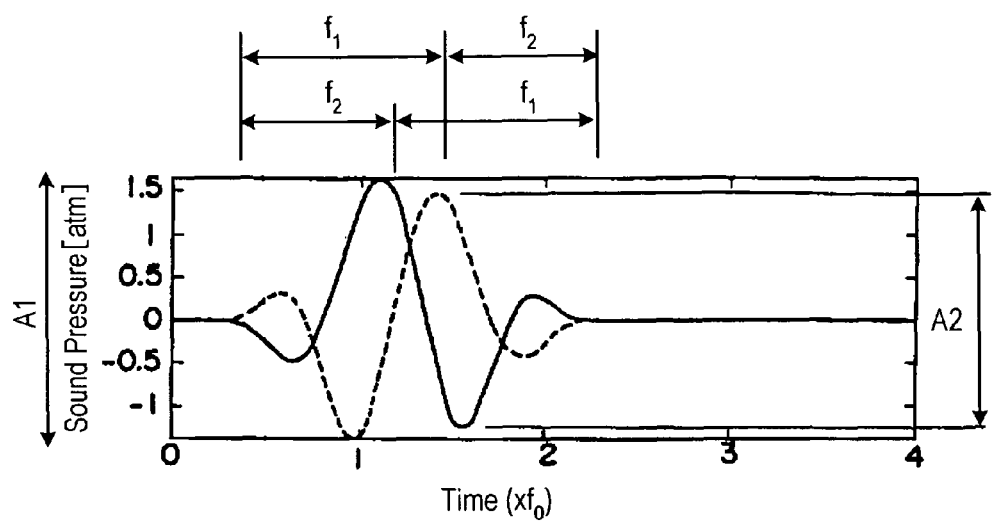
FIGS. 5a and 5b are graphs presenting the simulation results of waveforms of a transmitted signal and spectrums of the transmitted signal and a received signal in an ultrasound diagnostic apparatus according to a second embodiment of the present invention.
Figure 5B:
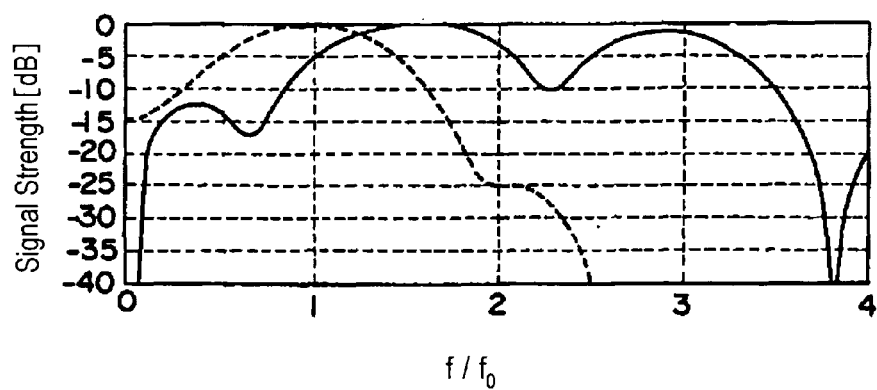

An example of the first waveform and the second waveform having a varying frequency and amplitude and the frequency spectrum of transmitted signal and received signal will be described with reference to FIGS. 5a and 5b showing the simulation results thereof. FIG. 5a is a graph presenting the first waveform and the second waveform, in which the horizontal axis indicates time and the vertical axis indicates sound pressure. In the graph, the first waveform is presented by a solid line and the second waveform is presented by a broken line. As shown in FIG. 5a, the first waveform is formed by joining a first cycle of frequency $f_1$ (=1.8 MHz) and a second cycle of frequency $f_2$ (=2.2 MHz), and, with its polarity, the sound pressure decreases at the start of the signal. On the other hand, the second waveform is formed by joining a first cycle of frequency $f_2$ and a second cycle of frequency $f_1$, and, with its polarity, the sound pressure increases. In both the first waveform and the second waveform, the amplitude A2 in the second cycle is set to be smaller than the amplitude A1 in the first cycle. For example, in the case of FIG. 5a, the amplitude is set as A2=0.9A1.

FIG. 5b is a graph presenting frequency spectrums of a transmitted signal and a received signal obtained by phasing and adding received signals respectively corresponding to the first waveform and the second waveform. Similar to FIG. 2b, the horizontal axis indicates the frequency ratio ($f/f_0$) in relation to $f_0=2.0$ MHz and the vertical axis indicates signal strength (dB). In FIG. 5(b), the spectrum of the transmitted signal is presented by a broken line, and the spectrum of a phased and added received signal is presented by a solid line.

As shown in FIG. 5b, the spectrum of transmitted wave resembles that shown in FIG. 3b. However, the signal strength in the vicinity of frequency $2f_0$ is −25 dB of the signal strength in the vicinity of $f_0$.

On the other hand, the spectrum of the phased and added received signal has its peaks where it becomes maximal in the vicinity of $0.4f_0$, $1.6f_0$, and $2.8f_0$, and has its nadirs where it becomes minimal in the vicinity of $0.7f_0$, $2.2f_0$, and $3.8f_0$. Among the maximal peaks, the signal strength is maximized at the peak in the vicinity of $1.6f_0$. Compared therewith, the signal strengths at the peaks in the vicinity of $0.4f_0$ and $2.8f_0$ are respectively about −13 dB and −2 dB. Meanwhile, the signal strengths at the nadirs in the vicinity of $0.7f_0$, $2.2f_0$, and $3.8f_0$ where the signal strength becomes minimal are respectively about −17 dB, −10 dB, and −40 dB or less.

As is clear by comparing FIG. 5b with FIG. 2b, the peak of the signal strength comes in the vicinity of $1.6f_0$ by shifting the frequency $f_1$ and frequency $f_2$ and shifting the amplitude A1 and amplitude A2, and the frequency spectrum shifts so as to be low.

Further, in the frequency spectrum according to this embodiment, difference $\Delta f$ between the frequency $f_1$ and the frequency $f_2$ is variably set in response to a predetermined transmission focus depth, and the ratio A2/A1 between the amplitude A1 and the amplitude A2 is also variably set. Specifically, as in the first embodiment, $\Delta f$ and A2/A1 are variably set so that the frequency spectrum of a signal obtained by combining received signals corresponding to the first waveform and the second waveform shifts so as to be low as the transmission focus depth becomes deeper.

As described above, according to this embodiment, the spectrum shift of the phased and added received signal can be emphasized by shifting the amplitude of the first waveform and the second waveform, in addition to the effect obtained by first embodiment described above.

Embodiment 3

Next, a third embodiment of the ultrasound diagnostic apparatus according to the present invention will be described. Here again, the same points as those enumerated in the description of the first embodiment will not be mentioned again, and only the differences will be described.

Figure 6:
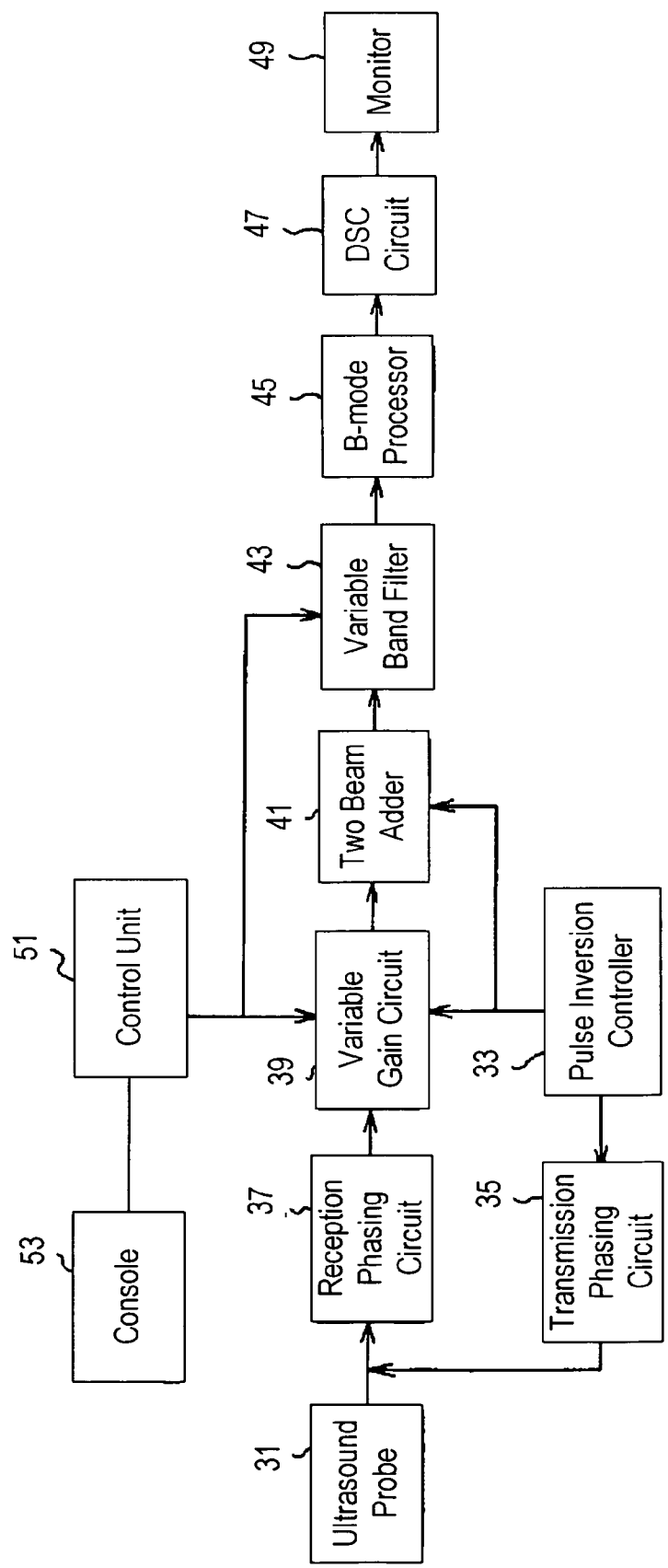
FIG. 6 is a block diagram showing the structure of an ultrasound diagnostic apparatus according to a third embodiment of the present invention.

FIG. 6 is a block diagram showing the structure of an ultrasound diagnostic apparatus according to this embodiment. As shown in FIG. 6, the ultrasound diagnostic apparatus includes an ultrasound probe 31 having a plurality of ultrasound transducers or an ultrasound transducer array (not shown), a pulse inversion control unit 33 for controlling a signal transmitted to an object to be examined (not shown) via the ultrasound probe 31, and a transmitted wave phasing circuit 35 for generating a transmitted wave in response to a command from the pulse inversion control unit 33 and the driving ultrasound probe 31. The transmission phasing circuit 35 has a transmission timing generating circuit, a transmission beam former circuit, and a transmission driver, which are not shown, and it is designed to supply a high-pressure transmitted signal to the ultrasound probe 31. At this time, the transmitted beam former circuit generates a beam forming signal for forming an ultrasound beam in a predetermined direction on the basis of the transmission timing signal generated by the transmission timing generating circuit. The beam forming signal includes a plurality of driving signals, each of which is given a time difference corresponding to the predetermined direction of the beam.

Further, the apparatus also includes a reception phasing circuit 37 for phasing and adding the signals received from the object via the ultrasound probe at each channel of the plurality of ultrasound transducers, a variable gain circuit 39 for amplifying or attenuating a signal output by the reception phasing circuit 37 depending on the variably determined gain, and a two beam adder unit 41 for temporarily storing an output signal of the variable gain circuit 39 and phasing and adding it with a signal output by the variable gain circuit 39 after a time interval. Further, the apparatus includes a variable band pass filter 43 for performing a digital band pass filter calculation on the output signal of two beam adder unit 41, a B-mode processing unit 45 for performing known B-mode image processings including detection, logarithmic compression, and enhancement processing on the basis of the output signal of the variable band pass filter 43, a DSC circuit 47, and a monitor 49 for displaying an image of video signals output by the DSC circuit 47. Further, the apparatus includes a control unit 51 for controlling the variable gain circuit 39 and variable band pass filter 43, and it is connected to a console 53 having an input means.

Meanwhile, the variable gain circuit 39 has a function of performing a known time gain control with variable gain on the plurality of signals received at time intervals in accordance with instructions from the pulse inversion control unit 33 and the control unit 51. Further, the variable band pass filter 43 has a reception dynamic filter function for variably setting the center frequency and the band width of the frequency pass band depending on the reception depth on the basis of a time control signal generated by the control unit 51.

Next, the operation of the above described ultrasound diagnostic apparatus will be described. In the ultrasound diagnostic apparatus according to this embodiment, the first waveform and second waveform are similar to those shown in FIG. 2$a$, i.e. the first waveform is formed by joining two waveforms of frequency $f_0$ and the second waveform is formed by time-inverting or polarity-inverting the first waveform, as in the conventional pulse inversion method. In the variable gain circuit 39, a time gain control is performed on received signals respectively corresponding to the first waveform and the second waveform in a reception timing of the received signals, i.e. with a gain (amplitude gain) different depending on the depth of the detecting portion. After that, those received signals are phased and added by the two beam adder unit 41 so as to be formed into one RF signal.

Figure 7:
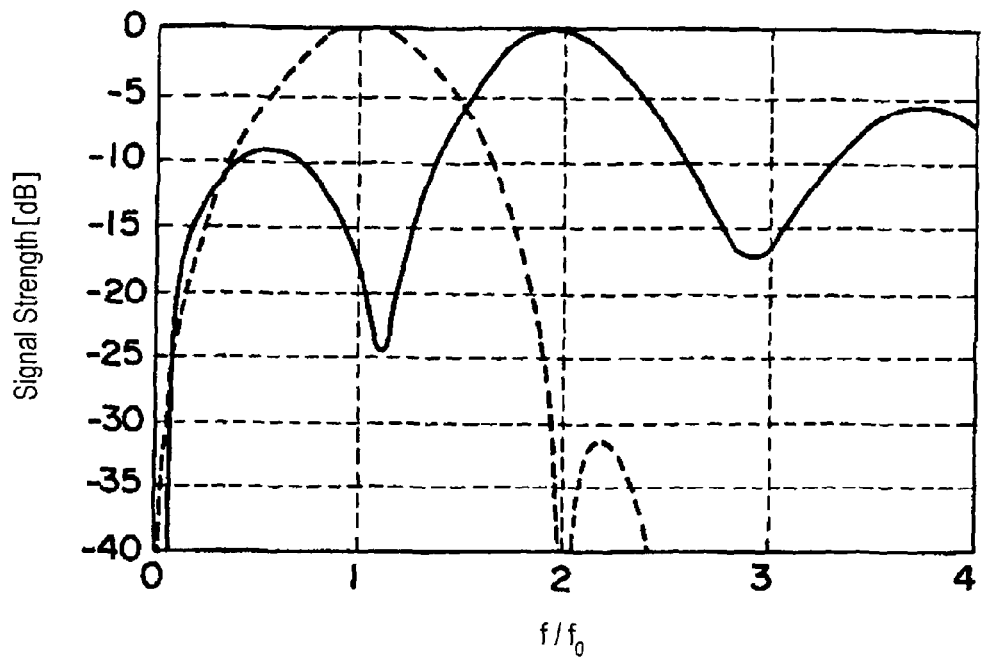
FIG. 7 is a graph presenting the simulation results of spectrums of a transmitted signal and a received signal in the ultrasound diagnostic apparatus according to the third embodiment of the present invention.
Figure 8:
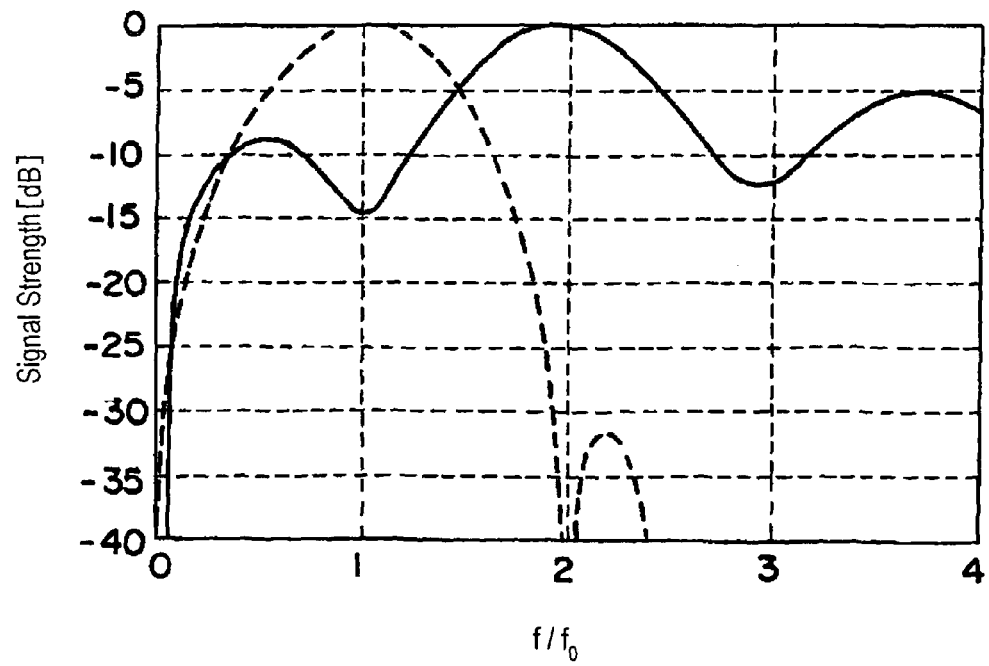
FIG. 8 is a graph presenting the simulation results of spectrums of a transmitted signal and a received signal in the ultrasound diagnostic apparatus according to the third embodiment of the present invention.
Figure 9:
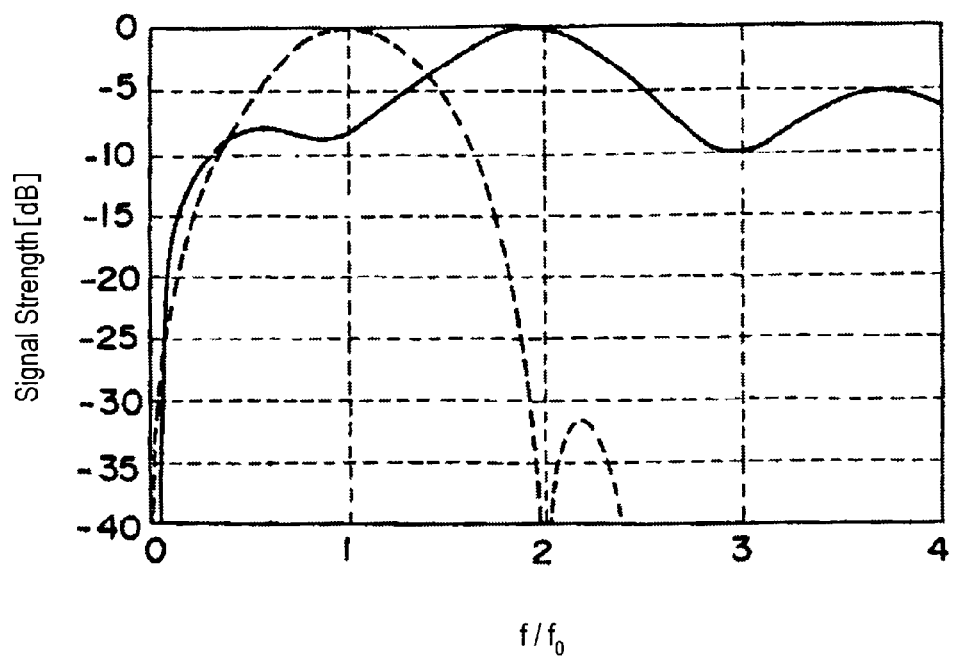
FIG. 9 is a graph showing the simulation results of spectrums of a transmitted signal and a received signal in the ultrasound diagnostic apparatus according to the third embodiment of the present invention.

FIGS. 7 to 9 are graphs showing the simulation results of the frequency spectrums of the transmitted signal and the combined received signal according to this embodiment, wherein the gain ratio between the received signals corresponding to the first waveform and the second waveform is 1:1, 1.2:0.8, and 1.35:0.65, respectively. In each figure, as in FIG. 2$b$, the horizontal axis indicates the frequency ratio ($f/f_0$) in relation to $f_0$=2 MHz and the vertical axis indicates signal strength (dB). The spectrum of the transmitted signal is represented by a broken line and that of received signal, after phasing and addition, is represented by a solid line. Meanwhile, needless to say, the spectrum of the transmitted signal here is the same as that shown in FIG. 2$b$.

Next, the spectrum of the received signal after phasing and addition in each figure will be described. FIG. 7 shows the case where a ratio of the gain (hereinafter referred to as "gain ratio") between received signals respectively corresponding to the first waveform and the second waveform is 1:1. As shown in FIG. 7, the spectrum of the received signal has its peaks where the signal strength becomes maximal in the vicinity of $0.6f_0$, $1.9f_0$, and $3.7f_0$. On the other hand, the spectrum has its nadirs where the signal strength becomes minimal in the vicinity of $1.1 f_0$ and $2.9f_0$. The signal strength is maximized at the peak in the vicinity of $1.9f_0$. In relation to this maximum signal strength, the signal strengths at other peaks and at the nadirs are about $-9$ dB, $-25$ dB, $-17$ dB, and $-6$ dB, respectively, in the vicinity of $0.6f_0$, $1.1f_0$, $2.9f_0$, and $3.7f_0$.

FIG. 8 shows the case where the gain ratio is 1.2:0.8. As shown in FIG. 8, the spectrum of the received signal has its peaks where the signal strength becomes maximal in the vicinity of $0.6f_0$, $1.9f_0$, and $3.7f_0$. On the other hand, the spectrum has its nadirs where the signal strength becomes minimal in the vicinity of $f_0$ and $2.9f_0$. The signal strength is maximized at the peak in the vicinity of $1.9f_0$. In relation to the maximum signal strength, the signal strengths at other peaks and at nadirs are about $-8$ dB, $-15$ dB, $-13$ dB, and $-5$ dB, respectively, in the vicinity of $0.6f_0$, $f_0$, $2.9f_0$, and $3.7f_0$.

FIG. 9 shows the case where the gain ratio is 0.35:0.65. As shown in FIG. 9, the spectrum of received signal has its peak where the signal strength becomes maximal in the vicinity of $0.6f_0$, $1.9f_0$, and $3.7f_0$. On the other hand, the spectrum has its nadirs where the signal strength becomes minimal in the vicinity of $0.9f_0$ and $2.9f_0$. The signal strength is maximized at the peak in the vicinity of $1.9f_0$. In relation to the signal strength at this time, the signal strengths at other peaks and at nadirs are $-8$ dB, $-9$ dB, $-10$ dB, and $-5$ dB respectively in the vicinity of $0.6f_0$, $0.9f_0$, $2.9f_0$, and $3.7f_0$.

As is clear by comparing FIG. 7, FIG. 8 and FIG. 9, the spectrum of the phased and added received signal is varied by changing the gain ratio. For example, when attention is focused on the component in a frequency band between $f_0$ and $2f_0$, it is more emphasized in FIG. 8 than in FIG. 7, and it is further emphasized in FIG. 9 than in FIG. 8. Meanwhile, in relation to the peak at $1.9f_0$, the signal strength at $1.5f_0$ is about $-7$ dB in FIG. 7, $-5$ dB in FIG. 8, and $-3$ dB in FIG. 9.

Further, according to this embodiment, the gain ratio is variably set in accordance with a predetermined reception focus depth. Specifically, the gain ratio is set to be larger as the reception focus depth becomes deeper. This change of gain ratio is sequentially carried out in the reception timing in conjunction with a known reception dynamic focus. That is, the time gain control is performed with different correlation curves between the reception timing and the gain on the received signals respectively corresponding to the first waveform and the second waveform.

Further, variable band pass filter 43 variably sets a frequency pass band depending on a predetermined reception focus depth. Specifically, the frequency pass band is set to be wide and the center frequency is set to be low in an area where the reception focus depth is shallow, and, thus, a secondary harmonic component is passed through a wide band. As the reception focus depth becomes deeper and the fundamental component is more emphasized, the frequency pass band of the variable band pass filter is set to be narrow and a floor frequency is set to be high, thereby the fundamental component is reduced.

As described above, according to this embodiment, the polarities of the first waveform and the second waveform are mutually inverted, and the received signals corresponding to the first waveform and of the second waveform are amplified or attenuated with a gain difference. In this manner, the frequency spectrum of the received signal after phasing and addition is varied, and a component in the frequency band between $f_0$ and $2f_0$ can be emphasized, whereby the penetration can be improved without lowering $F_0$ and deteriorating the resolution.

Further, since the gain difference and the frequency pass band of the variable band pass filter are variably set depending on the reception focus depth, in a relatively shallow portion the secondary harmonic component can be emphasized by canceling the fundamental component by setting the gain difference to be small or 0, or by setting the frequency pass band of the variable band pass filter to be wide. On the contrary, in a relatively deep portion, the penetration can be improved by setting the gain difference to be large, narrowing the frequency pass band, and setting the center frequency to be low.

Meanwhile, according to the above-described embodiment, the gains of both received signals corresponding to the first waveform and the second waveform are variably set. However, it is also possible that one gain is fixed and only the other is variably set. For example, it is possible that the gain of the first waveform is fixed as 1 and only the gain of the second waveform is variably set. Alternatively, the gain ratio may be variably set in stages as 1:1, 1:0.6, and then 1:0.3. Further, in addition to or instead of varying the gain of a received signal, the amplitude in transmission of the first waveform and the second waveform may be varied.

The invention claimed is:

1. An ultrasound diagnostic apparatus comprising:
   an ultrasound probe;
   a transmission unit for transmitting an ultrasound signal to an object to be examined via the ultrasound probe;
   a reception unit for processing a signal received by the ultrasound probe; and
   an image generating unit for generating a tissue harmonic image on the basis of the received signal processed by the reception unit,
   the transmission unit being configured to transmit an ultrasound signal including a first waveform and an ultrasound signal including a second waveform formed by time-inverting the first waveform, having varying frequency plural times in an identical direction at time intervals, and
   the reception unit being configured for phasing and adding the received signals respectively corresponding to the first waveform in which the frequency to increase and the second waveform in which the frequency to decrease,
   wherein:
   the transmission unit has a function of varying the first waveform so that the frequency sequentially increases and varying the second waveform so that the frequency sequentially decreases,
   the transmission unit being configured to variably set a transmission focus depth of the ultrasound signal, and
   a difference ($\Delta f$) between a frequency ($f_1$) in a first cycle and a frequency ($f_2$) in a second cycle, and a ratio ($A_2/A_1$) between an amplitude ($A_1$) in the first cycle and an amplitude ($A_2$) in the second cycle are variably set in response to a predetermined transmission focus depth.

2. An ultrasound diagnostic apparatus according to claim 1, wherein the shape of the first waveform and that of the second waveform are axisymmetrical about a line perpendicular to a time axis.

3. An ultrasound diagnostic apparatus according to claim 1, the first waveform and the second waveform vary respectively so that the signal strength is reduced.

4. An ultrasound diagnostic apparatus according to claim 1, wherein the transmission unit has a function of variably setting a transmission focus depth, and at least either a change rate of varying frequency of the first waveform and the second waveform or a change rate of varying signal strength of the first waveform and the second waveform is variably determined depending on the transmission focus depth.

5. An ultrasound diagnostic apparatus according to claim 1, wherein the reception unit has a filter for extracting a predetermined frequency band of the received signal, and the frequency band is variably set depending on the reception timing of the received signal.

6. An ultrasound diagnostic apparatus according to claim 1, wherein the frequency of the first waveform and/or the second waveform increases or decreases at every two or more cycles.

7. An ultrasound diagnostic apparatus according to claim 1, wherein the frequency of the first waveform and/or the second waveform increases or decreases at every one or less cycle.

8. An ultrasound diagnostic apparatus according to claim 1, wherein the frequency of the first waveform and/or the second waveform continuously increases or decreases.

9. An ultrasound diagnostic apparatus according to claim 1, wherein the reception unit has a function of phasing and adding the received signals corresponding to the first waveform and the second waveform while amplifying or attenuating them with a gain difference.

10. An ultrasound diagnostic apparatus comprising:
    an ultrasound probe;
    a transmission unit for transmitting an ultrasound signal to an object to be examined via the ultrasound probe;
    a reception unit for processing a signal received by the ultrasound probe; and
    an image generating unit for generating a tissue harmonic image on the basis of the received signal processed by the reception unit,
    the transmission unit being configured to transmit an ultrasound signal including a first waveform and an ultrasound signal including a second waveform formed by time-inverting the first waveform, having varying frequency plural times in an identical direction at time intervals, and
    the reception unit being configured for phasing and adding the received signals respectively corresponding to the first waveform in which the frequency to increase and the second waveform in which the frequency to decrease,
    wherein the transmission unit being configured to variably set a transmission focus depth of the ultrasonic signal, and
    wherein a difference ($\Delta f$) between a frequency ($f_1$) in a first cycle and a frequency ($f_2$) in a second cycle, and a ratio ($A_2/A_1$) between an amplitude ($A_1$) in the first cycle and an amplitude ($A_2$) in the second cycle are variably set in response to a predetermined transmission focus depth.

11. An ultrasound diagnostic apparatus according to claim 10, wherein a gain difference is variably set depending on a reception timing of the received signals.

12. An ultrasound diagnostic apparatus according to claim 10, wherein the transmission unit has a function of varying the first waveform so that the frequency sequentially decreases.

* * * * *